United States Patent
Dai et al.

(10) Patent No.: US 12,410,162 B2
(45) Date of Patent: Sep. 9, 2025

(54) PYRAZOLE ACYLHYDRAZONE CONTAINING TRIFLUOROMETHYLTHIADIAZOLE UNITS, PREPARATION METHOD AND USE THEREOF

(71) Applicant: NANTONG UNIVERSITY, Jiangsu (CN)

(72) Inventors: Hong Dai, Jiangsu (CA); Dandan Zheng, Jiangsu (CN); Heyi Miao, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 897 days.

(21) Appl. No.: 17/597,918

(22) PCT Filed: Jul. 1, 2021

(86) PCT No.: PCT/CN2021/103978
§ 371 (c)(1),
(2) Date: Jan. 28, 2022

(87) PCT Pub. No.: WO2022/002193
PCT Pub. Date: Jan. 6, 2022

(65) Prior Publication Data
US 2023/0348448 A1    Nov. 2, 2023

(30) Foreign Application Priority Data
Jul. 1, 2020   (CN) .......................... 202010622844.5

(51) Int. Cl.
*C07D 417/12*   (2006.01)
*A01N 43/82*   (2006.01)
*A01P 1/00*   (2006.01)
*C12Q 1/18*   (2006.01)

(52) U.S. Cl.
CPC ........... *C07D 417/12* (2013.01); *A01N 43/82* (2013.01); *A01P 1/00* (2021.08); *C12Q 1/18* (2013.01)

(58) Field of Classification Search
CPC ......... C07D 417/12; A01P 1/00; A01N 43/82; C12Q 1/18
See application file for complete search history.

(56) References Cited

PUBLICATIONS

Dai (Chin. J. Org. Chem. 2017, 37, 1542-1547) (Year: 2017).*

* cited by examiner

*Primary Examiner* — Kortney L. Klinkel
*Assistant Examiner* — Richard Grant Peckham
(74) *Attorney, Agent, or Firm* — McNees Wallace & Nurick LLC

(57) ABSTRACT

The present disclosure provides a preparation method and use of pyrazole acylhydrazone containing a trifluoromethylthiadiazole unit, which relates to the technical field of chemical pesticides. The pyrazole acylhydrazone containing a trifluoromethylthiadiazole unit provided by the present disclosure is obtained by the condensation of trifluoromethylthiadiazole hydrazide and pyrazole aldehyde. The pyrazole acylhydrazone containing a trifluoromethylthiadiazole unit has an excellent control effect on plant pathogens, and the compound can be used to prepare bactericides in the fields of agriculture, horticulture, etc.

17 Claims, No Drawings

PYRAZOLE ACYLHYDRAZONE CONTAINING TRIFLUOROMETHYLTHIADIAZOLE UNITS, PREPARATION METHOD AND USE THEREOF

CROSS REFERENCE TO RELATED APPLICATION

This patent application claims the benefit and priority of Chinese Patent Application No. 202010622844.5 filed on Jul. 1, 2020, the disclosure of which is incorporated by reference herein in its entirety as part of the present application.

TECHNICAL FIELD

The present disclosure relates to the technical field of chemical pesticides, in particular to a preparation method and use of pyrazole acylhydrazone containing a trifluoromethylthiadiazole unit.

BACKGROUND ART

The prevention and control of plant pathogens is one of the core areas of pesticide scientific research. The effective use of agricultural bactericides has enabled many plant pathogens to be effectively controlled. In recent years, certain plant pathogens have become resistant to traditional bactericides. Therefore, it is necessary for pesticide chemistry researchers to develop new types of bactericides.

Trifluoromethylthiadiazole compounds are an important class of compounds, which have a wide range of applications in agricultural production.

Pyrazole acylhydrazone derivatives are also an important class of compounds, and they also have important applications in plant protection.

Therefore, in order to further find new pyrazole acylhydrazone derivatives with good bactericidal activity from the pyrazole acylhydrazone compounds, and reasonably link the trifluoromethyl thiadiazole unit with the pyrazole acylhydrazone skeleton, the present disclosure discloses a kind of pyrazole acylhydrazone containing a trifluoromethyl thiadiazole unit with agricultural insecticidal application value.

SUMMARY

The purpose of the present disclosure is to provide a pyrazole acylhydrazone containing a trifluoromethylthiadiazole unit with excellent bactericidal effects against plant pathogens, so as to meet the demand for high-efficiency bactericides for crop protection.

Another object of the present disclosure is to provide a method for preparing the above compound.

Another object of the present disclosure is to provide the use of the above compounds in the preparation of bactericides.

In order to solve the above technical problems, according to the first aspect of the present disclosure, a pyrazole acylhydrazone containing a trifluoromethylthiadiazole unit is provided, which has a structure represented by general formula I,

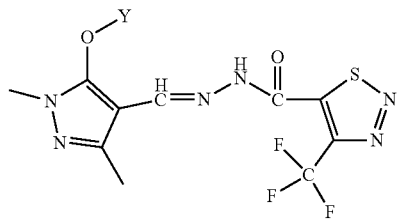

$Y=3\text{-}ClC_6H_4$, $3\text{-}BrC_6H_4$, $2,4\text{-}F_2C_6H_3$, $2,4\text{-}Cl_2C_6H_3$, etc.

In some embodiments, the pyrazole acylhydrazone containing a trifluoromethylthiadiazole unit has the following structure:

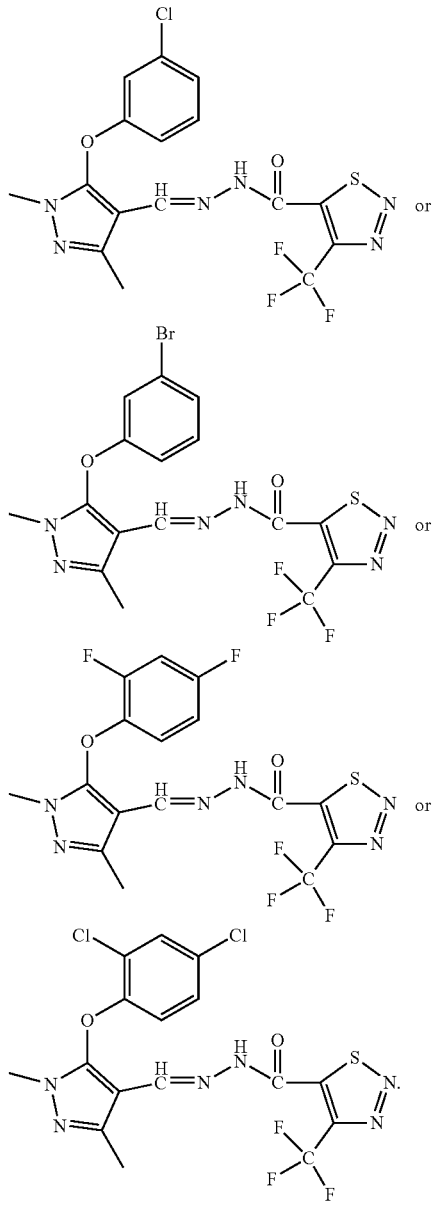

According to the second aspect of the present disclosure, a method for preparing the pyrazole acylhydrazone containing a trifluoromethylthiadiazole unit is provided, wherein comprising the following steps:

Dissolving compound II in an organic solvent, then adding compound III, after reacting for a period of time, and purifying the residue obtained after removing the solvent by column chromatography to obtain the target;

[Structure of Compound II: hydrazide with trifluoromethyl thiadiazole]

+

[Structure of Compound III: pyrazole with OY substituent and aldehyde] →(solvent)

[Structure of Compound I: pyrazole-acylhydrazone with trifluoromethyl thiadiazole]

Y = 3-ClC₆H₄, 3-BrC₆H₄, 2,4-F₂C₆H₃, 2,4-Cl₂C₆H₃

I

In some embodiments, the method for preparing the pyrazole acylhydrazone containing a trifluoromethylthiadiazole unit is as follows:

[Structure: hydrazide compound]

+

[Structure: 3-chlorophenoxy pyrazole aldehyde] →(t-C₄H₉OH)

[Structure: Compound Ia with 3-chlorophenoxy group]

Ia or

[Structure: hydrazide compound]

+

[Structure: 3-bromophenoxy pyrazole aldehyde] →(Toluene)

[Structure: Compound with 3-bromophenoxy group]

or

[Structure: hydrazide compound]

+

[Structure: 2,4-difluorophenoxy pyrazole aldehyde] →(1,4-Dioxane)

-continued

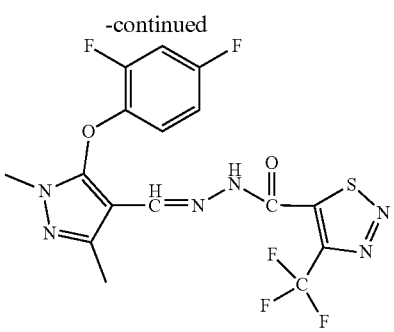

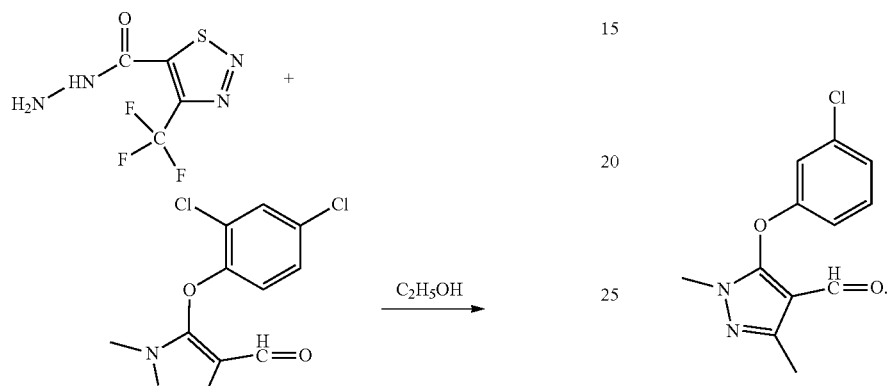

In some embodiments, when the structure of the pyrazole acylhydrazone containing a trifluoromethylthiadiazole unit is

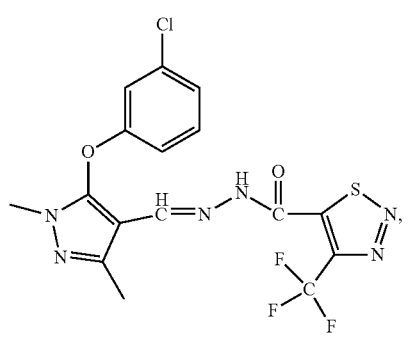

the method comprises the following steps:

Dissolving 5 mmol of intermediate II in 30 mL of tert-butanol, adding 5 mmol of intermediate IIIa thereto at room temperature, and then heating and refluxing for 26 h;

The structure of intermediate II is

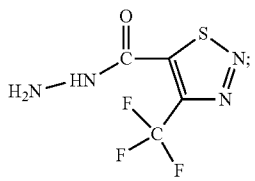 [SMILES: NNC(=O)c1snnc1C(F)(F)F]

The structure of intermediate IIIa is

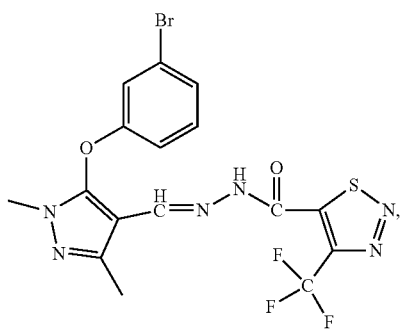 [SMILES: Cc1nn(C)c(Oc2cccc(Br)c2)c1/C=N/NC(=O)c1snnc1C(F)(F)F]

In some embodiments, when the structure of the pyrazole acylhydrazone containing a trifluoromethylthiadiazole unit is

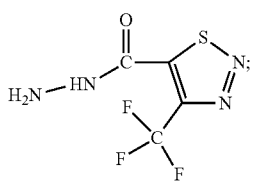 [SMILES: NNC(=O)c1snnc1C(F)(F)F]

the method comprises the following steps:

Dissolving 8 mmol of intermediate II in 35 mL of toluene, adding 10 mmol of intermediate IIIb thereto at room temperature, and heating and refluxing for 18 h;

The structure of intermediate II is

The structure of intermediate IIIb is

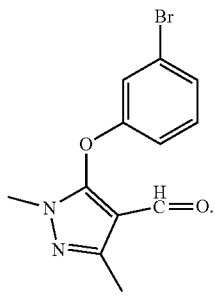 [SMILES: Cc1nn(C)c(Oc2cccc(Br)c2)c1C=O]

In some embodiments, when the structure of the pyrazole acylhydrazone containing a trifluoromethylthiadiazole unit is

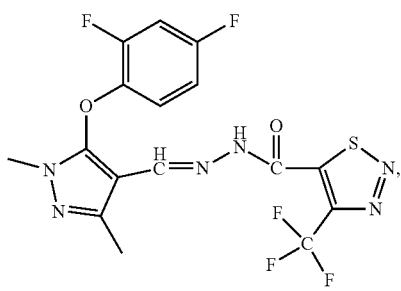 [SMILES: Cc1nn(C)c(Oc2ccc(F)cc2F)c1/C=N/NC(=O)c1snnc1C(F)(F)F]

the method comprises the following steps:

Dissolving 12 mmol of intermediate II in 60 mL of 1,4-dioxane, adding 16 mmol of intermediate IIIc thereto at room temperature, and then stirring at room temperature for 23 h;

The structure of intermediate II is

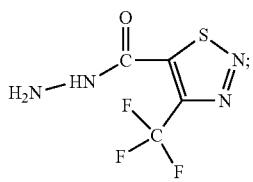

The structure of intermediate IIIc is

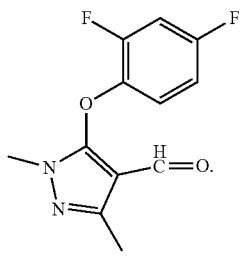 [SMILES: Cc1nn(C)c(Oc2ccc(F)cc2F)c1C=O]

In some embodiments, when the structure of the pyrazole acylhydrazone containing a trifluoromethylthiadiazole unit is

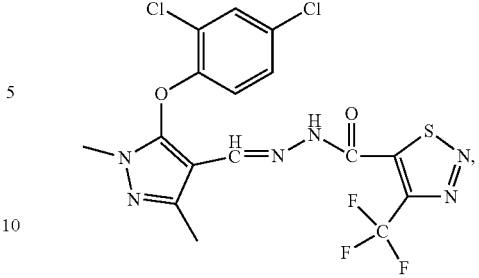

the method comprises the following steps:

Dissolving 7 mmol of intermediate II in 50 mL of ethanol, adding 9 mmol of intermediate IIId thereto at room temperature, and then heating and refluxing for 15 h;

The structure of intermediate II is

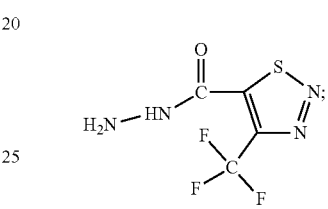

The structure of intermediate IIId is

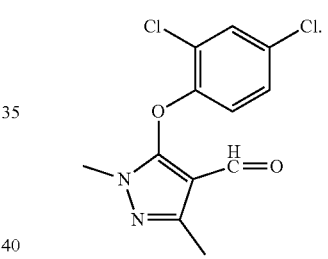

The present disclosure provides the use of the pyrazole acylhydrazone containing a trifluoromethylthiadiazole unit described in above technical schemes in the preparation of bactericides.

In some embodiments, the bactericide is a plant pathogen bactericide.

In some embodiments, the plant pathogens comprise *Mycosphaerella melonis*.

The present disclosure provides a bactericidal composition, comprising an active ingredient and a pesticide adjuvant; the active ingredient is the pyrazole acylhydrazone containing a trifluoromethylthiadiazole unit described in above technical scheme.

In some embodiments, the pesticide adjuvant is water, organic solvents, surface agents, and other adjuvants; and the other adjuvants are wetting agents and thickeners.

In some embodiments, the organic solvent is toluene, xylene, cyclohexanol, methanol, butanol, ethylene glycol, acetone, dimethylformamide, acetic acid, dimethyl sulfoxide, animal oil, vegetable oil, or fatty acid.

In some embodiments, the surfactant is an emulsifier and a dispersant.

In some embodiments, the surfactants are anionic surfactants, cationic surfactants, nonionic surfactants or amphoteric surfactants.

In some embodiments, the dosage form of the bactericidal composition is an emulsion in water, a suspension, a water dispersible granule or an emulsifiable concentrate.

In some embodiments, the mass content of the active ingredient in the bactericidal composition is 0.1-99.5%.

In some embodiments, when the dosage form is an emulsion in water, the mass content of the active ingredient in the emulsion in water is 5-50%;

When the dosage form is a suspension, the mass content of the active ingredient in the suspension is 5-40%.

The present disclosure provides a method of using the bactericidal composition described in above technical schemes, wherein the method of using is one or more of spraying on the stems and leafs, water surface application, soil treatment and seed treatment.

In some embodiments, when the method of using is spraying on the stems and leafs, the concentration of the active ingredient in the bactericidal composition is 1-1000 μg/mL.

In the present disclosure, the compound of general formula I has an excellent bactericidal effect on plant pathogens. Therefore, the compound of the present disclosure can be used to prepare bactericides to protect plants such as agriculture and horticulture. The plant pathogens include *Mycosphaerella melonis*. Of course, the harmful organisms that can be controlled by the compound of the present disclosure are not limited to the range exemplified above.

When the compound of the present disclosure represented by the general formula I is used as a bactericide in the fields of agriculture, horticulture, etc., it can be used alone or in the form of a bactericidal composition, e.g., formula I used as the active ingredient and the pesticide adjuvants commonly used in the field are processed into emulsions in water, suspensions, water dispersible granules, and emulsifiable concentrates.

Commonly used pesticide adjuvants include liquid carriers such as water; organic solvents such as toluene, xylene, cyclohexanol, methanol, butanol, ethylene glycol, acetone, dimethylformamide, acetic acid, dimethyl sulfoxide, animals and vegetable oils and fatty acids; commonly used surfactants such as emulsifiers and dispersants, including anionic surfactants, cationic surfactants, nonionic surfactants and amphoteric surfactants; other adjuvants, such as wetting agents, thickeners, etc.

When the compound of the present disclosure represented by the general formula I is used as an active ingredient in a bactericide, the content in the bactericide is selected in the range of 0.1%-99.5%, and the active ingredient content can be appropriately determined according to the formulation form and application method. Usually, the emulsion in water contains 5%-50% (weight percentage, the same below) of the active ingredient, preferably 10%-40%; the suspension contains 5%-50% of the active ingredient, preferably 5%-40%.

For the use of the bactericide of the present disclosure, common application methods can be selected, such as spraying on the stems and leafs, water surface application, soil treatment and seed treatment. For example, when spraying on the stems and leafs is used, the active ingredient of the compound represented by the general formula I can be used in emulsions in water, suspensions, water dispersible granules, emulsifiable concentrates in the concentration range of 1-1000 μg/mL, preferably 1-200 μg/mL.

The pyrazole acylhydrazone containing a trifluoromethylthiadiazole unit disclosed in the present disclosure exhibits an excellent bactericidal effect on plant pathogens, so it can be used to prepare bactericides used in agriculture, horticulture, etc.

DETAILED DESCRIPTION OF THE EMBODIMENTS

The above schemes will be further described below in conjunction with specific embodiments. It should be understood that these embodiments are used to illustrate the present disclosure and not to limit the scope of the present disclosure. The implementation conditions used in the examples can be further adjusted according to the conditions of specific manufacturers, and implementation conditions not specified are usually conditions in routine experiments.

Example 1

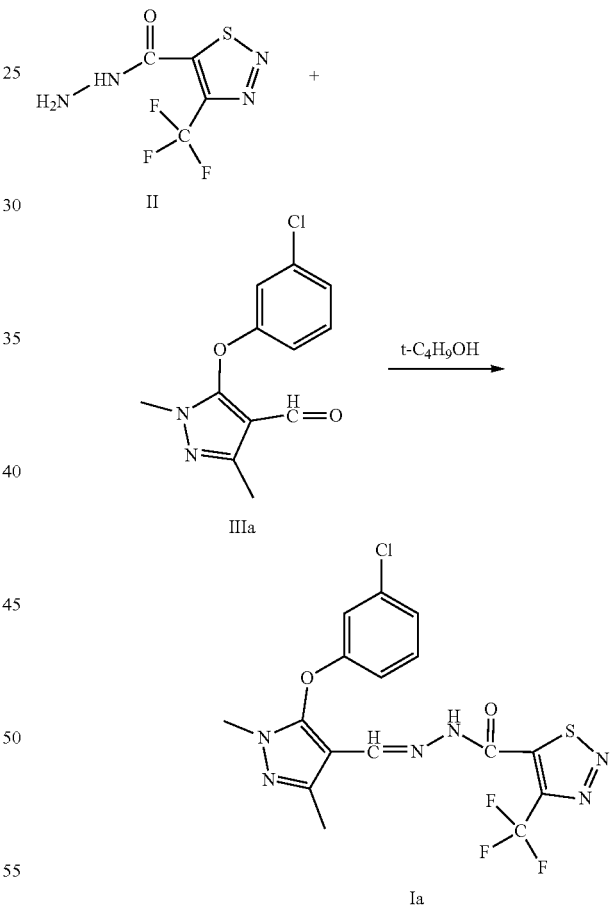

5 mmol of intermediate II was dissolved in 30 mL of tert-butanol, and 5 mmol of intermediate IIIa was added thereto at room temperature. Then the mixture was heated and refluxed for 26 h. The residue obtained after the solvent was removed by rotary evaporation was purified by column chromatography to obtain the target compound Ia; $^1$H NMR (CDCl$_3$, 400 MHz) δ: 10.39 (s, 1H, NH), 7.78 (s, 1H, CH=N), 6.79-7.18 (m, 4H, Ar—H), 3.61 (s, 3H, CH$_3$), 2.37 (s, 3H, CH$_3$).

Example 2

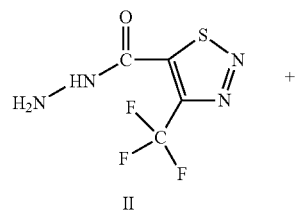

+

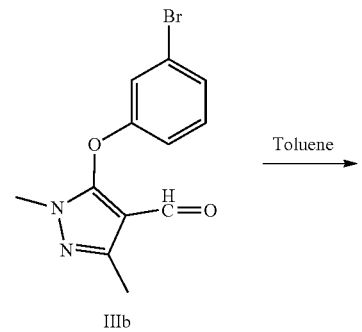

Toluene →

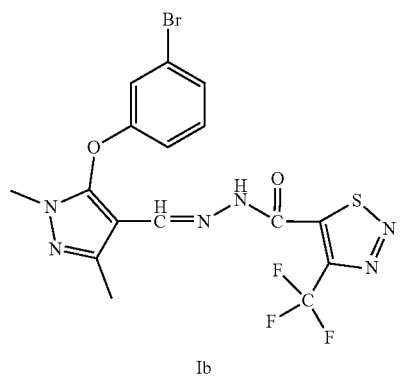

8 mmol of intermediate II was dissolved in 35 mL of toluene, and 10 mmol of intermediate IIIb was added thereto at room temperature. The reaction was heated and refluxed for 18 h. The residue obtained after the solvent was removed by rotary evaporation was purified by column chromatography to obtain the target compound Ib; $^1$H NMR (CDCl$_3$, 400 MHz) δ: 10.62 (s, 1H, NH), 7.80 (s, 1H, CH=N), 7.18-7.22 (m, 2H, Ar—H), 6.83-6.99 (m, 2H, Ar—H), 3.61 (s, 3H, CH$_3$), 2.38 (s, 3H, CH$_3$).

Example 3

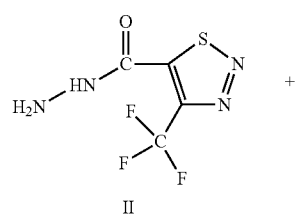

+

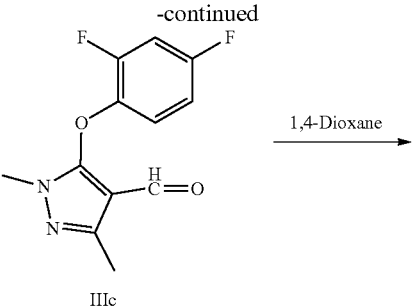

1,4-Dioxane →

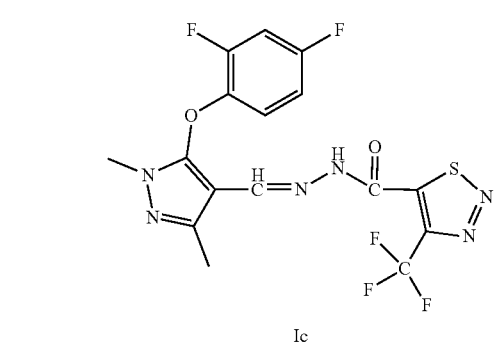

12 mmol of intermediate II was dissolved in 60 mL of 1,4-dioxane, and 16 mmol of intermediate IIIc was added thereto at room temperature. Then the mixture was stirred at room temperature for 23 h. The residue obtained after the solvent was removed by rotary evaporation was purified by column chromatography to obtain the target compound Ic; $^1$H NMR (CDCl$_3$, 400 MHz) δ: 10.63 (s, 1H, NH), 7.79 (s, 1H, CH=N), 6.68-7.00 (m, 3H, Ar—H), 3.64 (s, 3H, CH$_3$), 2.35 (s, 3H, CH$_3$).

Example 4

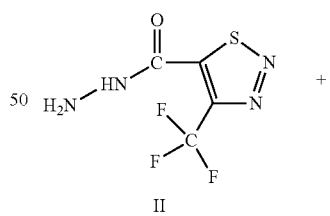

+

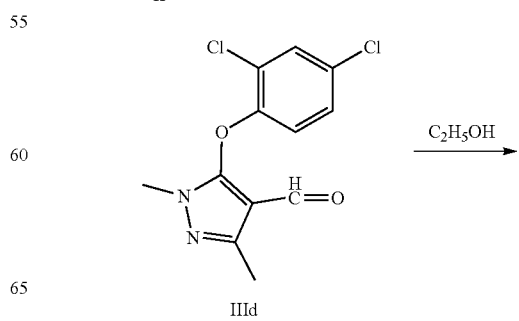

C$_2$H$_5$OH →

-continued

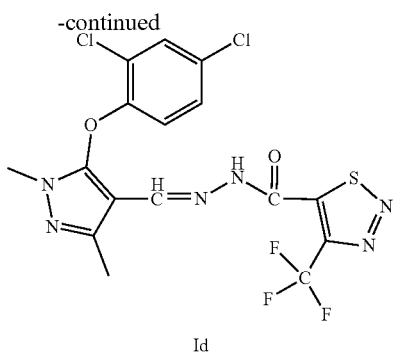

Id 7 mmol of intermediate II was dissolved in 50 mL of ethanol, and 9 mmol of intermediate IIId was added thereto at room temperature. Then the mixture was heated and refluxed for 15 h. The residue obtained after the solvent was removed by rotary evaporation was purified by column chromatography to obtain the target compound Id; $^1$NMR (CDCl$_3$, 400 MHz) δ: 11.30 (s, 1H, NH), 7.87 (s, 1H, CH=N), 7.49 (d, J=2.4 Hz, 1H, Ar—H), 7.10-7.13 (m, 1H, Ar—H), 6.57 (d, J=8.8 Hz, 1H, Ar—H), 3.61 (s, 3H, CH$_3$), 2.38 (s, 3H, CH$_3$).

Example 5

Screening of the Bactericidal Activity of the Samples Against *Mycosphaerella melonis*

The toxic medium method was used to determine the antibacterial activity of the target against *Mycosphaerella melonis*. First the drug solution was added to the culture medium, then the bacterial cake was placed on the culture medium, the petri dish was placed in a 24-26° C. incubator in the dark, and then cultured at a constant temperature. Then according to the growth rate of pathogenic bacteria, when the diameter of the control was to about 8 cm, the antibacterial rate % was calculated. The test concentration was 200 μg/mL (the drug solution with other concentrations was obtained by diluting the drug solution with the concentration of 200 μg/mL).

The antibacterial activity test data of the target compounds Ia-Id are listed in Table 1. It can be seen from Table 1 that the target compounds Ia-Id show excellent antibacterial effect on *Mycosphaerella melonis*. When the test concentration is 200 μg/mL, the inhibition ratio of the target compounds Ia, Ib, Ic and Id on *Mycosphaerella melonis* is 100%, 100%, 90% and 100%, respectively.

TABLE 1

Antibacterial activity test data of the target compounds Ia-Id

| target compound | concentration (μg/mL) | Mycosphaerella melonis (inhibition ratio, %) |
|---|---|---|
| I a | 200 | 100 |
| I b | 200 | 100 |
| I c | 200 | 90 |
| I d | 200 | 100 |

The above test results show that the trifluoromethylthiadiazole unit and the pyrazole acylhydrazone skeleton are linked together reasonably, and the obtained new pyrazole acylhydrazone derivatives have good antibacterial activity.

The basic principles, main features and advantages of the present disclosure have been shown and described above. Those skilled in the industry should understand that the present disclosure is not limited by the above examples. The above examples and descriptions only illustrate the principles of the present disclosure. The present disclosure will have various changes and improvements without departing from the spirit and scope of the present disclosure, and these changes and improvements fall within the scope of the claimed disclosure. The scope of protection claimed by the present disclosure is defined by the appended claims and their equivalents.

What is claimed is:

1. A pyrazole acylhydrazone containing a trifluoromethylthiadiazole unit, having a following structure:

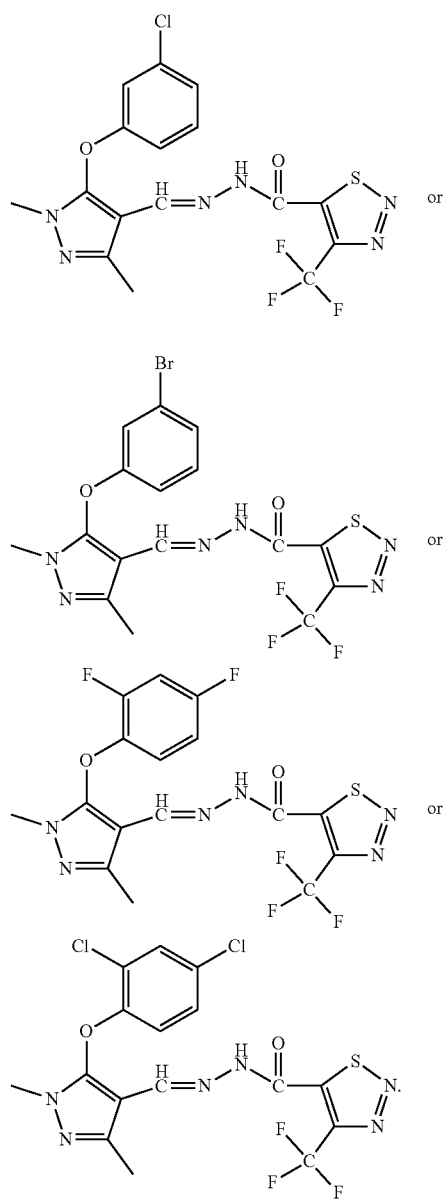

2. A method for preparing the pyrazole acylhydrazone containing the trifluoromethylthiadiazole unit according to claim 1, wherein the method is as follows:

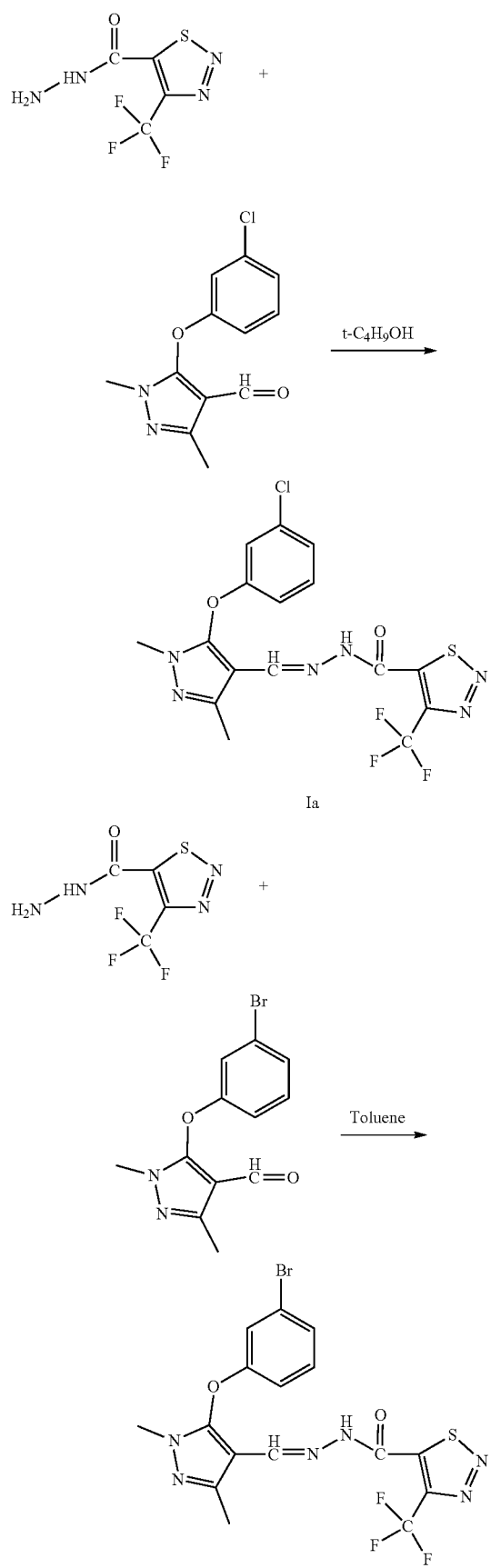
3. The method according to claim 2, wherein when a structure of the pyrazole acylhydrazone containing the trifluoromethylthiadiazole unit is

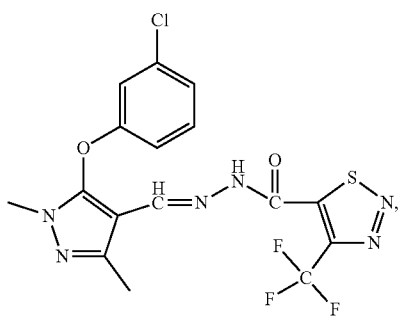 [SMILES: Cc1nn(C)c(Oc2cccc(Cl)c2)c1/C=N/NC(=O)c1snnc1C(F)(F)F]

the method comprises the following steps:

dissolving 5 mmol of intermediate II in 30 mL of tert-butanol, adding 5 mmol of intermediate IIIa thereto at room temperature, and then heating and refluxing for 26 h;

a structure of intermediate II is

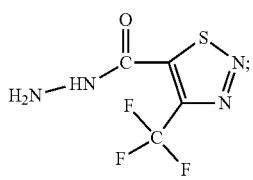

and a structure of intermediate IIIa is

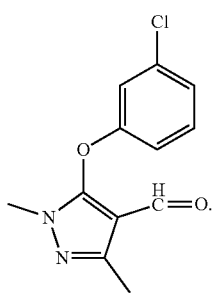 [SMILES: Cc1nn(C)c(Oc2cccc(Cl)c2)c1C=O]

4. The method according to claim 2, wherein when a structure of the pyrazole acylhydrazone containing the trifluoromethylthiadiazole unit is

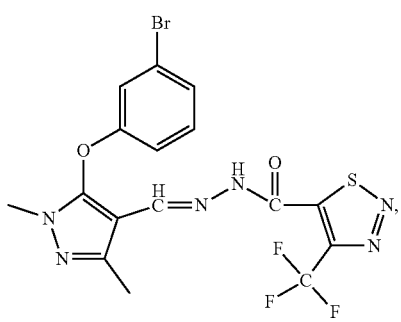 [SMILES: Cc1nn(C)c(Oc2cccc(Br)c2)c1/C=N/NC(=O)c1snnc1C(F)(F)F]

the method comprises the following steps:

dissolving 8 mmol of intermediate II in 35 mL of toluene, adding 10 mmol of intermediate IIIb thereto at room temperature, and heating and refluxing for 18 h;

a structure of intermediate II is

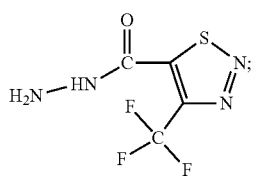 [SMILES: NNC(=O)c1snnc1C(F)(F)F]

and a structure of intermediate IIIb is

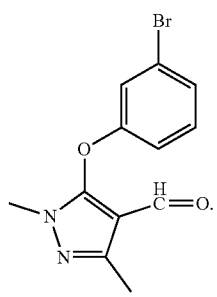 [SMILES: Cc1nn(C)c(Oc2cccc(Br)c2)c1C=O]

5. The method according to claim 2, wherein when a structure of the pyrazole acylhydrazone containing the trifluoromethylthiadiazole unit is

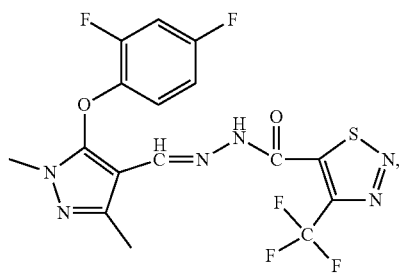 [SMILES: Cc1nn(C)c(Oc2ccc(F)cc2F)c1/C=N/NC(=O)c1snnc1C(F)(F)F]

the method comprises the following steps:

dissolving 12 mmol of intermediate II in 60 mL of 1,4-dioxane, adding 16 mmol of intermediate IIIc thereto at room temperature, and then stirring at room temperature for 23 h;

a structure of intermediate II is

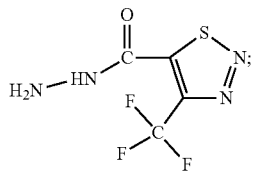 [SMILES: NNC(=O)c1snnc1C(F)(F)F]

and a structure of intermediate IIIc is

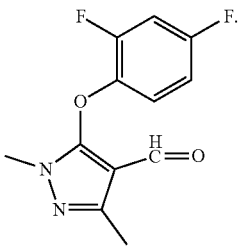 [SMILES: Cc1nn(C)c(Oc2ccc(F)cc2F)c1C=O]

6. The method according to claim 2, wherein when a structure of the pyrazole acylhydrazone containing the trifluoromethylthiadiazole unit is

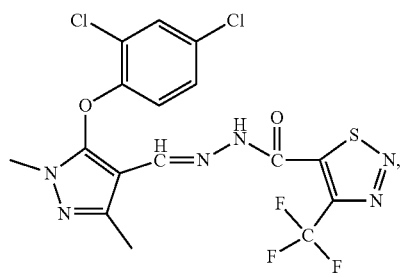

the method comprises the following steps:
dissolving 7 mmol of intermediate II in 50 mL of ethanol, adding 9 mmol of intermediate IIId thereto at room temperature, and then heating and refluxing for 15 h;
a structure of intermediate II is

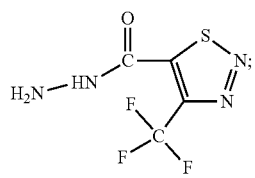

and
a structure of intermediate IIId is

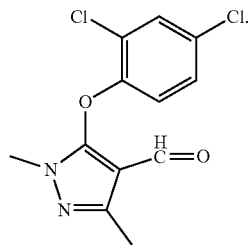 [SMILES: Cc1nn(C)c(Oc2ccc(Cl)cc2Cl)c1C=O]

7. A method for preparing the pyrazole acylhydrazone containing the trifluoromethylthiadiazole unit according to claim 1, wherein the method is as follows:
dissolving compound II in an organic solvent, then adding compound III, then reacting both compounds, and purifying a residue obtained after removing the organic solvent by column chromatography to obtain a target;

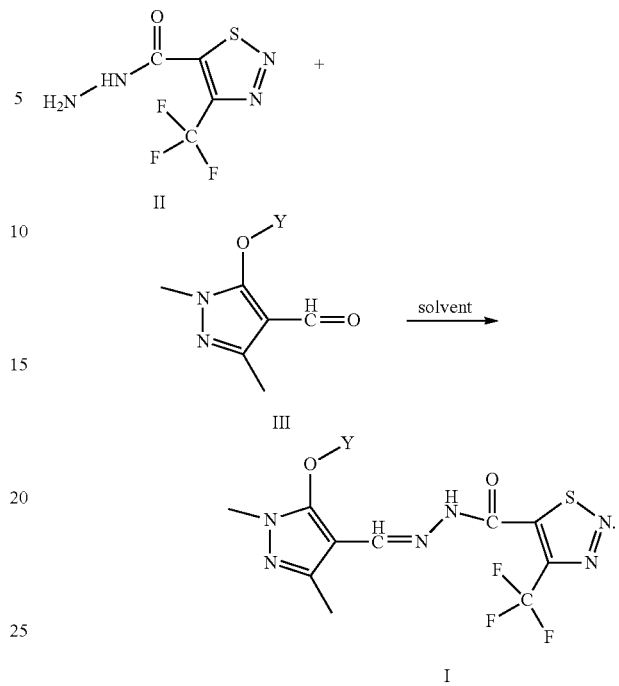

wherein Y represents 3-$ClC_6H_4$, 3-$BrC_6H_4$, 2,4-$F_2C_6H_3$, or 2,4-$Cl_2C_6H_3$.

8. A bactericidal composition, comprising an active ingredient and a pesticide adjuvant; wherein the active ingredient is the pyrazole acylhydrazone containing the trifluoromethylthiadiazole unit according to claim 1.

9. The bactericidal composition according to claim 8, wherein the pesticide adjuvant is selected from the group consisting of water, an organic solvent, a surfactant, and another adjuvant; and the other adjuvant is selected from the group consisting of a wetting agent and a thickener.

10. The bactericidal composition according to claim 9, wherein the organic solvent is selected from the group consisting of toluene, xylene, cyclohexanol, methanol, butanol, ethylene glycol, acetone, dimethylformamide, acetic acid, dimethyl sulfoxide, animal oil, vegetable oil, and fatty acid.

11. The bactericidal composition according to claim 9, wherein the surfactant is selected from the group consisting of an emulsifier and a dispersant.

12. The bactericidal composition according to claim 11, wherein the surfactant is selected from the group consisting of an anionic surfactant, a cationic surfactant, a nonionic surfactant, and an amphoteric surfactant.

13. The bactericidal composition according to claim 8, wherein a dosage form of the bactericidal composition is selected from the group consisting of an emulsion in water, a suspension, a water dispersible granule, and an emulsifiable concentrate.

14. The bactericidal composition according to claim 8, wherein a mass content of the active ingredient in the bactericidal composition is 0.1-99.5%.

15. The bactericidal composition according to claim 13, wherein when the dosage form is the emulsion in water, a mass content of the active ingredient in the emulsion in water is 5-50%; and
when the dosage form is the suspension, a mass content of the active ingredient in the suspension is 5-40%.

16. The bactericidal composition according to claim 9, wherein a dosage form of the bactericidal composition is selected from the group consisting of an emulsion in water, a suspension, a water dispersible granule, and an emulsifiable concentrate.

17. The bactericidal composition according to claim 16, wherein when the dosage form is the emulsion in water, a mass content of the active ingredient in the emulsion in water is 5-50%; and when the dosage form is the suspension, a mass content of the active ingredient in the suspension is 5-40%.

\* \* \* \* \*